United States Patent [19]

Alderman

[11] Patent Number: 4,734,285

[45] Date of Patent: Mar. 29, 1988

[54] SUSTAINED RELEASE COMPOSITIONS

[75] Inventor: Daniel A. Alderman, Midland, Mich.

[73] Assignee: The Dow Chemical Company, Midland, Mich.

[21] Appl. No.: 791,675

[22] Filed: Oct. 28, 1985

[51] Int. Cl.$^4$ .......................... A61K 9/22; A61K 47/00
[52] U.S. Cl. .................................... 424/468; 424/469; 424/470; 514/781; 514/965
[58] Field of Search .................. 514/781, 965; 424/19, 424/22, 468, 469, 470

[56] References Cited

U.S. PATENT DOCUMENTS

| | | | |
|---|---|---|---|
| 3,951,821 | 4/1976 | Davidson | 514/781 |
| 4,107,288 | 8/1978 | Oppenheim et al. | 424/22 |
| 4,126,672 | 11/1978 | Sheth et al. | 424/22 |
| 4,140,755 | 2/1979 | Sheth et al. | 514/781 |
| 4,167,558 | 9/1979 | Sheth et al. | 514/781 |
| 4,259,314 | 3/1981 | Lowey | 424/19 |
| 4,269,859 | 5/1981 | Morse | 514/781 |
| 4,369,172 | 1/1983 | Schor et al. | 514/781 |
| 4,389,393 | 6/1983 | Schor et al. | 514/781 |
| 4,477,657 | 10/1984 | Strange et al. | 536/91 |
| 4,528,125 | 7/1985 | Alderman et al. | 252/522 A |
| 4,540,566 | 9/1985 | Davis et al. | 424/22 |
| 4,571,333 | 2/1986 | Hsiao et al. | 424/22 |

FOREIGN PATENT DOCUMENTS

| | | | |
|---|---|---|---|
| 2050701 | 5/1971 | Fed. Rep. of Germany | 514/781 |
| 2518270 | 3/1976 | Fed. Rep. of Germany | 514/781 |
| 56-57719 | 5/1981 | Japan | 514/781 |
| 59-193815 | 11/1984 | Japan | 514/781 |
| 1405088 | 9/1975 | United Kingdom | 514/781 |

OTHER PUBLICATIONS

Solomon, "Importance of the Technology and Formulation on the Mechanism of Potassium Chloride Release, When Contained in a Hydrophilic Matrix"; 54, *Pharmaceutical Acta Helvetica*, pp. 86–89 (1979).

*Primary Examiner*—Ronald W. Griffin

[57] ABSTRACT

The release of an active composition from a solid tablet can be delayed by employing a fine particle sized hydroxypropyl methylcellulose ether composition.

8 Claims, No Drawings

SUSTAINED RELEASE COMPOSITIONS

BACKGROUND OF THE INVENTION

This invention relates to sustained release tablets, and particularly to such tablets comprised of a fine particle sized hydrophilic polymeric composition.

Polymeric compositions have been widely used as a matrix base for compressed tablets. Such tablets typically contain a medicament or a vitamin whose rate of release into the system is delayed or controlled by the matrix base. Controlled release tablets are desirable because they provide a method of delivering a long-lasting dose in a single application without overdosing the system.

Typically, an effective amount of the polymeric matrix composition is employed. It is desirable to employ as little amount of polymeric composition as possible to provide the intended release profile, to obtain minimum dosage size or to obtain good compression properties. For such applications, a highly hydrophilic polymeric composition is suitably employed. Such a composition rapidly hydrates and forms a gel-like layer in the tablet through which the dosage composition is released to the system. An example of a preferred hydrophilic polymeric composition is a cellulose ether sold as METHOCEL® K4M and K15M by The Dow Chemical Company, which has a hydroxypropoxyl substitution of between about 4 to about 12 weight percent, and a methoxyl substitution of between about 19 to about 25 weight percent.

In U.S. Pat. No. 4,369,172 it is disclosed that hydroxypropyl methylcellulose ethers having a hydroxypropoxyl content of from 9 to 12 percent and a number average molecular weight of less than about 50,000 provides the best sustained release. Moreover, the effect of hydration and gel formation is de-emphasized in favor of the chemical composition of the hydroxypropyl methylcellulose.

Cellulose ethers, such as METHOCEL® K, are desirable polymeric matrix compositions because they are derived from naturally occurring cellulose, and are free-flowing, readily compressible powders. Unfortunately, not all cellulose ethers hydrate rapidly, and therefore do not provide a desirable release profile for compressed tablets.

Yet another factor affecting the performance of the tablet is the chemical characteristics of the drug employed. Certain polymers can be employed beneficially for some drugs, but not for others. The degree of water-solubility of the drug, the drug's molecular weight and the diffusion coefficient in a hydrated polymer gel layer can be critical.

It would be desirable to have additional cellulose ether polymeric matrix materials which would provide sufficient release profiles for compressed tablets.

SUMMARY OF THE INVENTION

This invention is a process for providing delayed release solid tablets of a therapeutically active composition. The process comprises intimately mixing an amount of the active composition in the form of a powder with a functionally effective amount of a fine particle sized, substantially water-soluble hydroxypropyl methylcellulose ether composition. The cellulose ether composition is in the form of a powder, has a hydroxypropoxyl substitution of from about 7 to about 12 weight percent, a methoxyl substitution of from about 28 to about 30 weight percent, and a number average molecular weight of at least about 15,000. The intimate admixture is subjected to pressure conditions to form a solid tablet. The cellulose ether composition is sufficiently fine that the release of active composition from the solid tablet is delayed longer upon contacting an aqueous acidic environment at 37° C., compared to a tablet formulated with a chemically identical but coarser cellulose ether composition.

This invention is useful in providing compressed solid tablets of a therapeutically active composition and cellulose ether composition which exhibits sustained release of the active composition.

DETAILED DESCRIPTION OF THE INVENTION

The hydroxypropyl methylcellulose ether composition of this invention is within the USP specification for HPMC 2910. It has a hydroxypropoxyl substitution of from about 7 to about 12 weight percent, a methoxyl substitution of from about 28 to about 30 weight percent, and a number average molecular weight of at least about 15,000 or a 2 percent aqueous solution viscosity of at least 20 cps. Preferably, the cellulose ether has a number average molecular weight of at least about 50,000 or a 2 percent aqueous solution viscosity of at least 800 cps. Most preferably, the cellulose ether has a number average molecular weight of at least about 80,000 or a 2 percent aqueous solution viscosity of at least 3,000 cps. Such a cellulose ether hydrates most rapidly and forms a thick viscous gel which can delay the release of active composition.

Typically, the cellulose ether is prepared by the reaction of cellulose pulp with caustic to form alkali cellulose. The alkali cellulose is then reacted under control conditions with an alkyl halide and alkylene oxide to form the cellulose ether. Such a process is described, for example, in U.S. Pat. No. 4,477,657.

The cellulose ether composition useful in this invention has a sufficiently fine particle size that the release of active composition from a solid tablet is delayed longer upon contacting an aqueous acidic environment at 37° C.; compared to the release from a solid tablet formulated with a chemically identical but coarser particle sized cellulose ether composition. A cellulose ether composition is chemically identical, for purposes of this invention, when it possesses hydroxypropoxyl and methoxyl substitution within the ranges of USP HPMC 2910, and has a 2 percent aqueous solution viscosity within about 50 percent of the viscosity of the fine particle sized composition. A cellulose ether composition is coarse when the particle size distribution has a larger amount by weight of larger particles than the fine particle sized cellulose ether composition. A fine particle size is sufficient to increase the rate of hydration, and thereby delay the release of the active composition. Such particle size can vary, and typically is sufficient when about 90 weight percent of the cellulose ether composition, and preferably at least about 95 weight percent, can pass through a 100 mesh screen. More preferably, the cellulose ether has a particle size sufficient that at least about 95 weight percent, and most preferably at least about 97 weight percent can pass through a 140 mesh screen, although any size sufficient to form a gel-like layer can be employed.

The cellulose ether composition is substantially water-soluble. Substantially water-soluble refers to a composition which tends to spontaneously disperse its molecules throughout the molecules of water.

A functionally effective amount of the cellulose ether composition is employed. Such amount is an amount sufficient to delay the release of the therapeutically active composition. Preferably, the amount employed is the minimum amount required to provide the delayed release. Such an amount can vary and typically ranges from about 5 to about 90 percent, preferably from about 5 to about 25 percent, and most preferably from about 10 to about 17 percent based on weight of the tablet, although any functionally effective amount can be employed.

The therapeutically active composition is any composition which can be administered orally to affect a condition such as, for example, a pharmaceutical drug or vitamin. The active composition can be a water-soluble or a water-insoluble composition. A water-soluble composition is a composition which spontaneously disperses its molecules in an aqueous medium, and a water-insoluble composition is a composition which does not exhibit that spontaneous dispersion. Suitable water-soluble compositions include aspirin, theophylline, pseudoephedrine HCl, ascorbic acid, riboflavin, 5 phosphate sodium and the like. Suitable water-insoluble compositions include naproxyn and ibuprofen. Water-soluble compositions especially find the process of the invention useful because they tend to dissolve and diffuse through the hydrated cellulose ether layer, during gel formation.

The therapeutically active composition is employed in any effective dosage amount. Such amount is an amount sufficient to affect the condition to be treated. The amount can vary according to the specific active composition employed, and such variations are within the knowledge of the skilled artisan. Typically, the active composition can be employed up to about 95 weight percent of the compressed tablet, although any effective weight percent can be employed.

Typically, tablets can contain one or more optional compositions or excipients such as diluents or fillers, binders, lubricants and glidants. Diluents or fillers are compositions which can provide bulk and binding properties. Examples of suitable diluents or fillers are lactose, mannitol and the like. Typically, such diluents or fillers can be employed in the formulation up to about 80 weight percent, and preferably up to about 60 weight percent. Binders are compositions which can bind the components of the tablets together and are typically employed in a wet granulation process. Examples of suitable binders are hydroxypropyl methylcellulose, hydroxypropyl cellulose, starch and polyvinylpyrrolidinone. Typically, such binders are employed in from about 3 to about 8 weight percent. Lubricants are compositions which can prevent sticking to die walls or punch faces. Examples of suitable lubricants are magnesium stearate, stearic acid and the like. Typically, such lubricants are employed in an amount from about 0.5 to 3.0 weight percent. Glidants are compositions which can aid powder flow. An example of a suitable glidant is fumed silica. Typically, such glidants are employed in an amount from about 0.1 to 3.0 weight percent.

The active composition, polymer and optional ingredients are uniformly mixed together in powder form to provide a homogeneous mixture. The mixture is then subjected to compression to provide a solid tablet. Before compressing, the mixture can be subjected to a wet or dry granulation process. The powder or granulated mixture is fed to the die of a tablet press and sufficient pressure is applied to form a solid tablet. Such pressure can vary, and typically ranges from about 1,000 psi to about 6,000 psi, and preferably about 2,000 psi force. A solid tablet can substantially retain its form under conventional storage and handling conditions. The tablet also maintains its solid form upon administration, and provides sustained release of the active composition through diffusion and erosion.

Advantageously, the mixture of tablet ingredients can be treated in a dry granulation process or a wet granulation process. In a dry granulation process, the mixture is precompressed and milled into the desired size prior to tableting. In a wet granulation process, the mixture is combined and formed into granules with a polymeric binder solution and then sized and/or dried at the desired particle size prior to tableting. The size of the granulated mixture is not critical to the drug release rate. The release rate is affected, according to this invention, by the particle size of the cellulose ether composition prior to granulating.

The tablets are suitable for administering a therapeutically active composition to humans. Upon contacting the aqueous acidic environment typically present in humans, the tablets slowly dissolve. Typically, the acidic environment is provided by gastric juices, and is at about 37° C.

Solid tablets formulated with the small particle size cellulose ether composition of this invention surprisingly have a longer release profile compared to tablets formulated with a chemically identical cellulose ether composition which has a larger particle size distribution. When the cellulose ether composition has a particle size sufficiently small that at least about 97 weight percent can pass through a 140 mesh screen, the tablets typically require at least one hour, preferably at least two hours, and more preferably at least four hours longer to release the active composition compared to tablets formulated with a chemically identical cellulose ether composition having a particle size in which less than 97 weight percent can pass through a 140 mesh screen.

The following examples are illustrative only, and are not intended to limit the scope of the invention.

EXAMPLE 1

A 780 mg tablet of aspirin is made in a 0.5-inch concave punch at 3,000 pounds compaction force. The tablet formulation is 82.6 percent aspirin 100 mesh crystals, 16.5 percent METHOCEL ® E-50 Premium (i.e., HPMC 2910 USP, 50 cps), and 0.9 percent magnesium stearate lubricant. The HPMC is ball milled for 24 hours to reduce the particle size. About 95 percent of the HPMC passes through a 100 mesh screen. The tablet is placed in a USP dissolution device using the paddle method at 100 rpm in 0.1N HCl at 37° C. The release profile is provided in Table I, as Sample 1.

Comparative Sample 1*

An aspirin tablet is prepared using the same amounts and ingredients employed in Example 1, except that the same HPMC is not ball milled, and about 84 percent of the particles fail to pass through a 100 mesh screen. The tablet is placed in the same USP dissolution device as in Example 1. The release profile is provided in Table I as C-1*.

TABLE I

| Time (Hours) | Sample 1[1] (Percent) | C-1*[1] (Percent) |
|---|---|---|
| 0 | 0 | 0 |
| 0.5 | 13.2 | 95.9 |
| 1.0 | 18.4 | 100 |
| 1.5 | 22.7 | — |
| 2.0 | 30.6 | — |
| 3.0 | 38.2 | — |
| 5.0 | 54.3 | — |
| 7.0 | 71.5 | — |
| 9.0 | 100 | — |

*Not an example of this invention.
[1] The amount of aspirin released into the environment.

This example illustrates the difference in release profiles provided to a formulation by employing a small particle sized (Sample 1) versus a large particle sized (C-1*) cellulose ether composition as the release agent.

EXAMPLE 2

Aspirin tablets are prepared using the amounts and ingredients of Example 1. The cellulose ether (HPMC 2910, 50 cps) has the following particle size distribution.

| Mesh Size | Percent of HPMC Retained |
|---|---|
| +60 | 0.88 |
| +80 | 1.07 |
| +100 | 2.34 |
| +140 | 12.30 |
| +200 | 16.11 |
| +325 | 28.61 |
| thru −325 | 36.23 |

Tablets are prepared using the fraction which passes through the 140 mesh screen. The release profile is provided in Table II, under "Sample 2". Comparative tablets are prepared using the entire range of particle sizes. The release profile of these tablets is provided in Table II, under C-2*.

TABLE II

| Time Hours | Sample 2 (Percent) | C-2* (Percent) |
|---|---|---|
| 0 | 0 | 0 |
| 0.5 | 29.6 | 95.9 |
| 1.0 | 53.8 | 100 |
| 1.5 | 71.8 | — |
| 2.0 | 80.3 | — |
| 3.0 | 87.2 | — |
| 5.0 | 100 | — |

*Not an example of this invention.

This example illustrates the surprising benefits of employing a cellulose ether which exclusively has a small particle size (Sample 2) versus the release profile provided by a formulation employing a small amount (about 16 percent) of larger particle size (C-2*).

EXAMPLE 3

Solid tablets are prepared from a formulation of 52.6 percent lactose, 26.7 percent theophylline USP, 20.0 percent METHOCEL® E-4M Premium (HPMC 2910, USP) and 0.7 percent magnesium stearate. The tablet is a 750 mg tablet and is made using a 0.5-inch concave punch at about 3,000 psi compressional force. About 99 percent of the particles of the cellulose ether pass through a 100 mesh screen. The release profile is determined in the same dissolution device and environment used in Examples 1 and 2. The release profile is provided in Table III, under Sample 3.

Comparative Sample 3*

Tablets of theophylline are prepared in the same formulation as in Example 3. The cellulose ether composition has a substantially larger particle size (about 85 percent fail to pass through a 140 mesh screen). The release profile is measured as in Example 3, and is provided in Table 3, under C-3*.

TABLE III

| Time (Hours) | Sample 3 (Percent) | C-3* (Percent) |
|---|---|---|
| 0 | 0 | 0 |
| 0.5 | 17 | 21 |
| 1.5 | 21 | 38 |
| 3.0 | 35 | 55 |
| 5.0 | 47 | 69 |
| 7.0 | 59 | 80 |
| 9.0 | 67 | 92 |
| 11.0 | 77 | 100 |
| 13.0 | 81 | — |

*Not an example of this invention.

This example illustrates that smaller particle size can extend the sustained release properties of tablets which typically exhibit an effective sustained release profile.

What is claimed is:

1. A process for providing sustained release solid tablets of a therapeutically active composition, the process comprising
   (a) comminuting a substantially water-soluble hydroxypropyl methylcellulose ether, having a hydroxypropoxyl substitution of from about 7 to about 12 weight percent, a methoxyl substitution of from about 28 to about 30 weight percent, and a number average molecular weight of at least 50,000, to a relatively fine particle sized cellulose ether composition, having a 2% aqueous solution viscosity of at least 800 cps and wherein at least 90% by weight of the cellulose ether particles can pass through a 100 mesh screen; and
   (b) intimately mixing an amount of the active composition in the form of a powder with a functionally effective amount of the fine particle sized cellulose ether composition; and
   (c) subjecting the mixture of active composition and fine particle sized cellulose ether composition to compression conditions to form a solid tablet.

2. The process of claim 1, wherein at least 95 percent by weight of the cellulose ether particles can pass through a 100 mesh screen.

3. The process of claim 2, wherein at least 95 percent by weight of the cellulose ether particles can pass through a 140 mesh screen.

4. The process of claim 3, wherein at least 97 percent by weight of the cellulose ether particles can pass through a 140 mesh screen.

5. The process of claim 1, wherein an amount of a lubricant composition is mixed with the active composition and cellulose ether composition.

6. The process of claim 5, wherein the active composition is present up to about 95 weight percent of the tablet, the cellulose ether composition is present from about 5 to about 90 weight percent of the tablet, and the lubricant is present from about 0.5 to about 3 weight percent of the tablet.

7. The process of claim 6, wherein the compression conditions comprise subjecting the mixture of active composition, cellulose ether, and lubricant to between about 1,000 psi to about 6,000 psi.

8. The process of claim 7, wherein the cellulose ether composition has a 2 percent aqueous solution viscosity of at least 3,000 cps.

* * * * *